United States Patent
Donfried et al.

(10) Patent No.: US 9,384,330 B2
(45) Date of Patent: Jul. 5, 2016

(54) PROVIDING USER ATTRIBUTES TO COMPLETE AN ONLINE TRANSACTION

(75) Inventors: Paul A. Donfried, Richmond, MA (US);
Peter S. Tippett, Great Falls, VA (US);
Guy S. Tallent, Jr., New York, NY (US);
Ashley Evans, Stonington, CT (US)

(73) Assignee: VERIZON PATENT AND LICENSING INC., Basking Ridge, NJ (US)

(*) Notice: Subject to any disclaimer, the term of this patent is extended or adjusted under 35 U.S.C. 154(b) by 777 days.

(21) Appl. No.: 13/316,251

(22) Filed: Dec. 9, 2011

(65) Prior Publication Data

US 2013/0152155 A1    Jun. 13, 2013

(51) Int. Cl.
| G06F 21/00 | (2013.01) |
|---|---|
| H04L 29/06 | (2006.01) |
| G06Q 20/12 | (2012.01) |
| G06Q 30/00 | (2012.01) |
| G06Q 30/06 | (2012.01) |
| G06Q 50/22 | (2012.01) |

(52) U.S. Cl.
CPC ............... *G06F 21/00* (2013.01); *G06Q 20/12* (2013.01); *G06Q 30/00* (2013.01); *G06Q 30/06* (2013.01); *G06Q 50/22* (2013.01); *H04L 63/0815* (2013.01); *H04L 63/10* (2013.01)

(58) Field of Classification Search
USPC ........ 705/50, 16, 21, 51, 59, 71; 380/44, 262, 380/278, 279
See application file for complete search history.

(56) References Cited

U.S. PATENT DOCUMENTS

| 2008/0222543 | A1* | 9/2008 | Naono | G06F 17/30569 715/764 |
|---|---|---|---|---|
| 2008/0307500 | A1* | 12/2008 | Garnier | H04L 63/0853 726/3 |
| 2009/0163183 | A1* | 6/2009 | O'Donoghue | G06Q 30/02 455/414.1 |
| 2010/0023412 | A1* | 1/2010 | Kitagawa | G06Q 30/0601 705/26.1 |
| 2011/0060800 | A1* | 3/2011 | Cohen | G06Q 10/107 709/206 |
| 2011/0137804 | A1* | 6/2011 | Peterson | G06Q 20/085 705/77 |
| 2013/0144731 | A1* | 6/2013 | Baldwin | G06Q 20/20 705/17 |

* cited by examiner

*Primary Examiner* — Dante Ravetti (57) ABSTRACT

A first server device receives a request for attributes, of a user, from a second server device associated with a receiving entity. The first server device determines whether the receiving entity is entitled to receive the attributes, and authenticates an identity of the user. The first server device also identifies the attributes based on the identity when the receiving entity is entitled to receive the attributes, and transmits the identified attributes to the second server device.

9 Claims, 8 Drawing Sheets

| Receiving Entity Identifier | Example Company |
| Type of Receiving Entity | Online Beverage Retailer |
| Types of Transactions | Online Sale of Alcohol |
| Attributes Required for Transactions | 1) Age of User<br>2) Billing Information<br>3) Residential Address |

410 — Verified General Identity Attributes

| | |
|---|---|
| Legal Name | John E. Smith |
| Age | 35 |
| Gender | Male |
| Residential Address | 1600 Example Street, Washington, DC 20037 |
| City of Birth | Saint Paul, MN |
| Citizenship | USA |

420 — Consumer Attributes

| | |
|---|---|
| Payment Information | Example Credit Card; 1234 5678 9201 5214; 09/12; 452 |
| Billing Address | 1600 Example Street, Washington, DC 20037 |

430 — Employment Attributes

| | |
|---|---|
| Employer Identifier | Example Hospital |
| Type of Employer | Healthcare Provider |
| Employee Identifier | 256 |
| Job Title | Cardiologist |
| Work Email Address | jsmith@example.com |
| Office Address | 2450 Example Street, Washington, DC 20037 |

440 — Professional Attributes

| | |
|---|---|
| Medical License No. & State | 60 123456; DC |
| DEA Number | AJ 3274658 |
| Certifications/Credentials | |
| Specialties | Heart Bypass Surgery |

FIG. 4A

| Self-Asserted General Identity Attributes | |
|---|---|
| Legal Name | John Smith |
| Age | 65 |
| Gender | Male |
| Residential Address | 1600 Example Street, Washington, DC 20037 |
| City of Birth | Waterloo, IA |
| Citizenship | USA |

450

| Self-Asserted Preferences | |
|---|---|
| News Interests | Information Technology; Politics |
| Type of Shopping Preference | On-Line Shopping; Wholesale Retailers |
| Product Interests | Beverages; IT Products |
| Vacation Interests | All-Inclusive Resorts; Europe |
| Recreational Interests | Hiking |

PROVIDING USER ATTRIBUTES TO COMPLETE AN ONLINE TRANSACTION

BACKGROUND

Users are increasingly participating in online transactions, such as online shopping. To complete an online transaction, a user needs to provide attributes (e.g., an age, an address, billing information, etc.) of the user to a receiving entity relying on the attributes (e.g., an online merchant). However, the receiving entity can request for the user to provide more attributes than are necessary to process the online transaction. As a result, the receiving entity may mishandle private information of the user, which the receiving entity did not need to process the online transaction. A user also has to reenter information for attributes for each new online transaction with a new receiving entity with whom the user does not have a pre-existing online relationship. Furthermore, a receiving entity is often unable to ensure that attributes provided by a user are accurate.

DETAILED DESCRIPTION OF PREFERRED EMBODIMENTS

The following detailed description refers to the accompanying drawings. The same reference numbers in different drawings may identify the same or similar elements.

An attribute may refer to any information associated with a particular person. A policy may refer to information that specifies which types of attributes of a user may be needed for a particular receiving entity, associated with the policy, to complete/process an online transaction between a user (e.g., a customer) and the particular receiving entity. A receiving entity may refer to any entity that provides an online service via, for example, a website associated with the entity. A receiving entity may include, for example, an online merchant, a service provider (e.g., a health care provider), a government agency, etc. The online service may include, for example, online shopping, providing information (e.g., medical records), an online portal (e.g., online bank account portal), etc.

An implementation, described herein, may provide, to a receiving entity, attributes of a user that may be necessary to complete an online transaction. For example, a user may use a computer device to access a website of a receiving entity. The user may initiate an online transaction via the website. A server of the receiving entity may transmit a request for attributes of the user to an attributes server. The attributes server may retrieve a policy associated with the receiving entity. Based on the policy, the attributes server may determine whether the receiving entity is entitled to the requested attributes. If the attributes server determines that the receiving entity is entitled to the requested attributes, the attributes server may authenticate an identity of the user based on information (e.g., an Internet protocol (IP) address associated with a browser used to access the website) included in the request. After authenticating the identity of the user, the attributes server may retrieve verified attributes requested by the receiving entity. The attributes server may transmit the verified attributes to the server of the receiving entity. The server of the receiving entity may process/complete the online transaction based on the verified attributes.

Such implementations allow a user to avoid providing unnecessary attributes and/or to avoid re-entering information, as attributes, when initiating online transactions with a receiving entity. The implementations further allow the receiving entity to ensure that attributes used for the online transactions are accurate.

Figure 1:
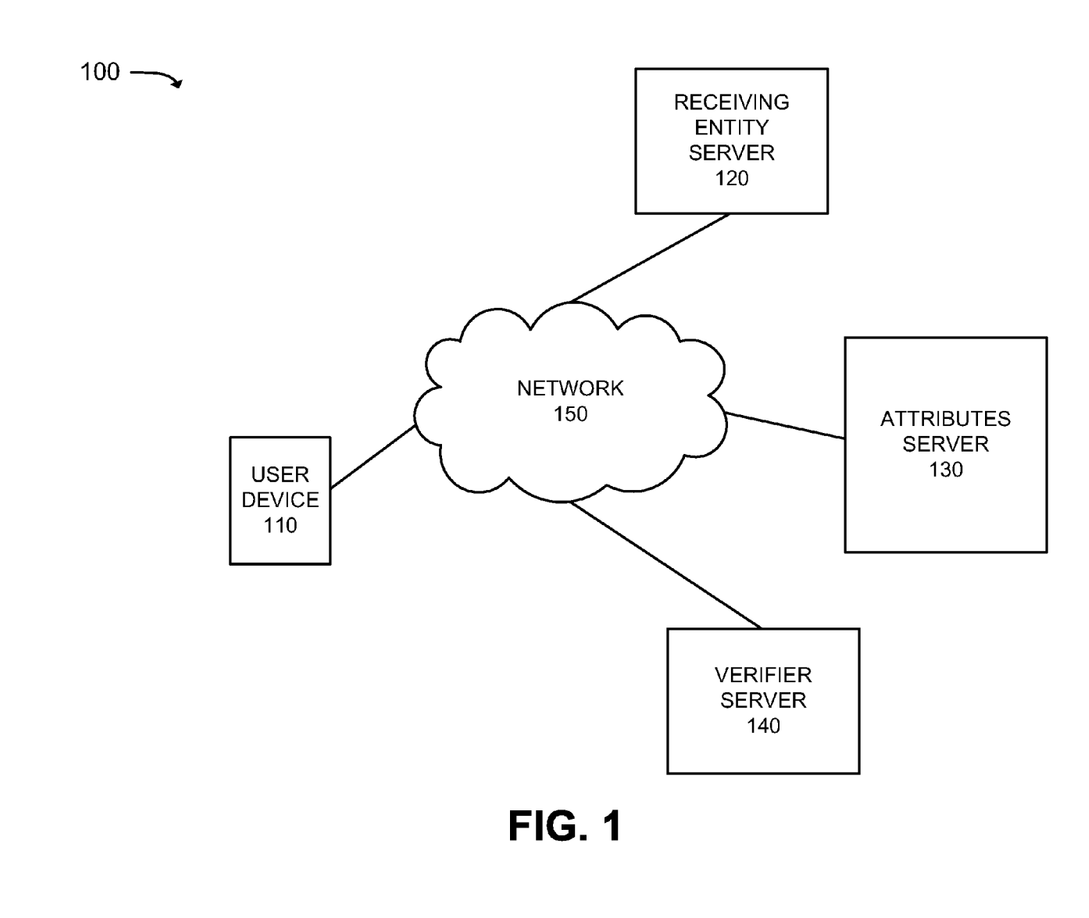
FIG. 1 is a diagram of an example environment in which systems and/or methods described herein may be implemented.

FIG. 1 is a diagram of an example environment 100 in which a system and/or method described herein may be implemented. As shown in FIG. 1, environment 100 may include one or more of the following components: a user device 110, a receiving entity server 120, an attributes server 130, a verifier server 140, and a network 150. A single user device 110, receiving entity server 120, attributes server 130, verifier server 140, and network 150 have been illustrated in FIG. 1 for simplicity. In practice, there may be more user devices 110, receiving entity servers 120, attributes servers 130, verifier servers 140, and/or networks 150. Also, in some implementations, one or more of the components of environment 100 may perform one or more functions described as being performed by another one or more of the components of environment 100.

Furthermore, two or more of the components, of FIG. 1, may be implemented within a single device, or a single component may be implemented as multiple, distributed devices. Also, components of environment 100 may interconnect via wired and/or wireless connections. In other words, any two components, of environment 100, may communicate via a wired connection, a wireless connection, or a combination of a wired connection and a wireless connection.

User device 110 may include any computation or communication device, such as a communication device that is capable of communicating with receiving entity server 120 via network 150. In one implementation, user device 110 may take the form of any computer, including a web service terminal, a personal computer, a laptop computer, a handheld computer, etc. Alternatively, or additionally, user device 110 may take the form of a mobile telephone device, including a smart phone, a personal digital assistant (PDA), etc. Alternatively, or additionally, user device 110 may take the form of a set-top box (STB) or any other device capable of transmitting and/or receiving data.

User device 110 may allow a user to open a browser and access a website of a receiving entity (e.g., provided by receiving entity server 120) via the browser. User device 110 may further allow the user to initiate an online transaction with the receiving entity via the website. User device 110 may receive, from attributes server 130, an authentication request to authenticate an identity of the user. The user may use user device 110 to provide authentication information (e.g., a username and a password) in response to the authentication request. User device 110 may transmit the authentication information to attributes server 130. User device 110 may receive, from receiving entity server 120, confirmation that the online transaction has successfully been processed/completed.

Receiving entity server 120 may include any computation or communication device, such as a communication device that is capable of communicating with user device 110 and/or attributes server 130 via network 150. Receiving entity server 120 may represent a single server device or a collection of multiple server devices and/or computer systems. Receiving entity server 120 may host a website associated with a receiving entity. Receiving entity server 120 may handle an online transaction initiated at user device 110 by a user of user device 110. An online transaction may include, for example, an online purchase, a request for information (e.g., medical records), a request to access an online portal (e.g., online bank account portal), etc.

In one implementation, receiving entity server 120 may generate a request to receive one or more attributes of the user to process/complete the online transaction. Alternatively, or additionally, receiving entity server 120 may generate a request to confirm one or more attributes of the user that were provided by the user, via user device 110, to receiving entity server 120. Receiving entity server 120 may transmit the request to attributes server 130. In response, receiving entity server 120 may receive one or more of the requested attributes, a confirmation that one or more of the provided attributes are accurate, and/or a message that receiving entity server 120 is not entitled to receive one or more of the requested attributes and/or a confirmation for one or more of the requested attributes.

Attributes server 130 may include any computation or communication device, such as a communication device that is capable of communicating with user device 110, receiving entity server 120, and/or verifier server 140 via network 150. Attributes server 130 may represent a single server device or a collection of multiple server devices and/or computer systems. In one implementation, a telecommunications service provider may operate attributes server 130. Alternatively, or additionally, any other entity that has access to policies associated with relying parties (e.g., including an operator of receiving entity server 120) and attributes associated with users (e.g., including a user of user device 110) may operate attributes server 130.

A receiving entity (e.g., an online merchant) associated with receiving entity server 120 may establish a service relationship with an operator of attributes server 130. In one implementation, the receiving entity and/or receiving entity server 120 may provide a type of the receiving entity and/or types of online transactions processed by receiving entity server 120. Attributes server 130 may perform due diligence to confirm the type of the receiving entity and/or the types of online transactions. Alternatively, or additionally, attributes server 130 may automatically determine the type of the receiving entity and/or the types of online transactions based on an identifier (e.g., a name of a business, a DUN & BRADSTREET identification number (i.e., a D-U-N-S Number), etc) provided by the receiving entity and/or receiving entity server 120.

Thereafter, attributes server 130, and or the operator of attributes server 130, may perform due diligence to determine which types of attributes are required by receiving entity server 120, for receiving entity server 120 to process online transactions, based on the type of the receiving entity and/or the types of online transactions. Attributes server 130 may create a policy for receiving entity server 120 and/or for the receiving entity based on the types of attributes that are required by receiving entity server 120. Attributes server 130 may interrogate the policy whenever attributes server 130 receives a request for attributes, or a request to confirm attributes, from receiving entity server 120.

To perform due diligence and/or to automatically determine information associated with a receiving entity (e.g., type of a receiving entity, types of online transactions processed by receiving entity server 120, types of attributes are required by receiving entity server 120, etc.), attributes server 130 may, for example, transmit messages (e.g., confirmation requests) to servers of third parties (e.g., DUN & BRADSTREET) (not shown in FIG. 1) that verify and/or provide information about different businesses and/or organizations. Attributes server 130 may confirm and/or determine the information based on responses from the servers of the third parties. Attributes server 130 may also store and/or have access to information about attributes required by different types of receiving entity and/or for different types of online transactions. Attributes server 130 may use the aforementioned information to determine types of attributes that are required by receiving entity server 120 based on a type of a receiving entity and/or a type of online transaction associated with receiving entity server 120.

A user of user device 110 may select types of attributes that attributes server 130 is allowed to provide about the user. In one implementation, attributes server 130 may request verified attributes, of the selected types, for the user from one or more verifier servers (e.g., including verifier server 140) based on service level agreements (SLAs) with third party data providers that operate the one or more verifier servers. For example, a user may select for attributes server 130 to provide a medical license number of the user when necessary. Attributes server 130 may retrieve/verify the medical license number every thirty days based on an SLA with a third party data provider that provides a verified medical license number of the user to attributes server 130.

Alternatively, or additionally, attributes server 130 may receive self-asserted attributes of the user (i.e., from user device 110 and/or from another computer device accessed by the user). Attributes server 130 may verify whether a self-asserted attribute provided by the user matches a verified attribute for the same type of attribute (e.g., age). Attributes server 130 may store a self-asserted attribute and a verified attribute for the same type of attribute. For example, a user may assert that she is 23 years old. Attributes server 130 may determine, based on information provided from verifier server 140, that a verified age attribute of the user is 38 years old. Attributes server 130 may store, for the user, a self-asserted age attribute of 23 years old and the verified age attribute of 38 years old.

Verifier server 140 may include any computation or communication device, such as a communication device that is capable of communicating with attributes server 130 via network 150. Verifier server 140 may represent a single server device or a collection of multiple server devices and/or computer systems. Verifier server 140 may collect and/or have access to a particular type of data (e.g., demographic data, credit card information, etc.). Verifier server 140 may be operated by a third party data provider, including, for example, LEXIS NEXIS, CHOICEPOINT, EXPERIAN, etc. Verifier server 140 may provide attributes of users to attributes server 130 based on SLAs with an operator of attributes server 130.

Network 150 may include a single network, multiple networks of a same type, or multiple networks of different types. For example, network 150 may include one or more of a direct connection between devices, a local area network (LAN), a wide area network (WAN) (e.g., the Internet), a metropolitan area network (MAN), a wireless network (e.g., a general packet radio service (GPRS) network), a telephone network (e.g., a Public Switched Telephone Network (PSTN) or a cellular network), a subset of the Internet, an ad hoc network, a fiber optic network (e.g., a fiber optic service (FiOS) network), or any combination of the aforementioned networks.

Figure 2:
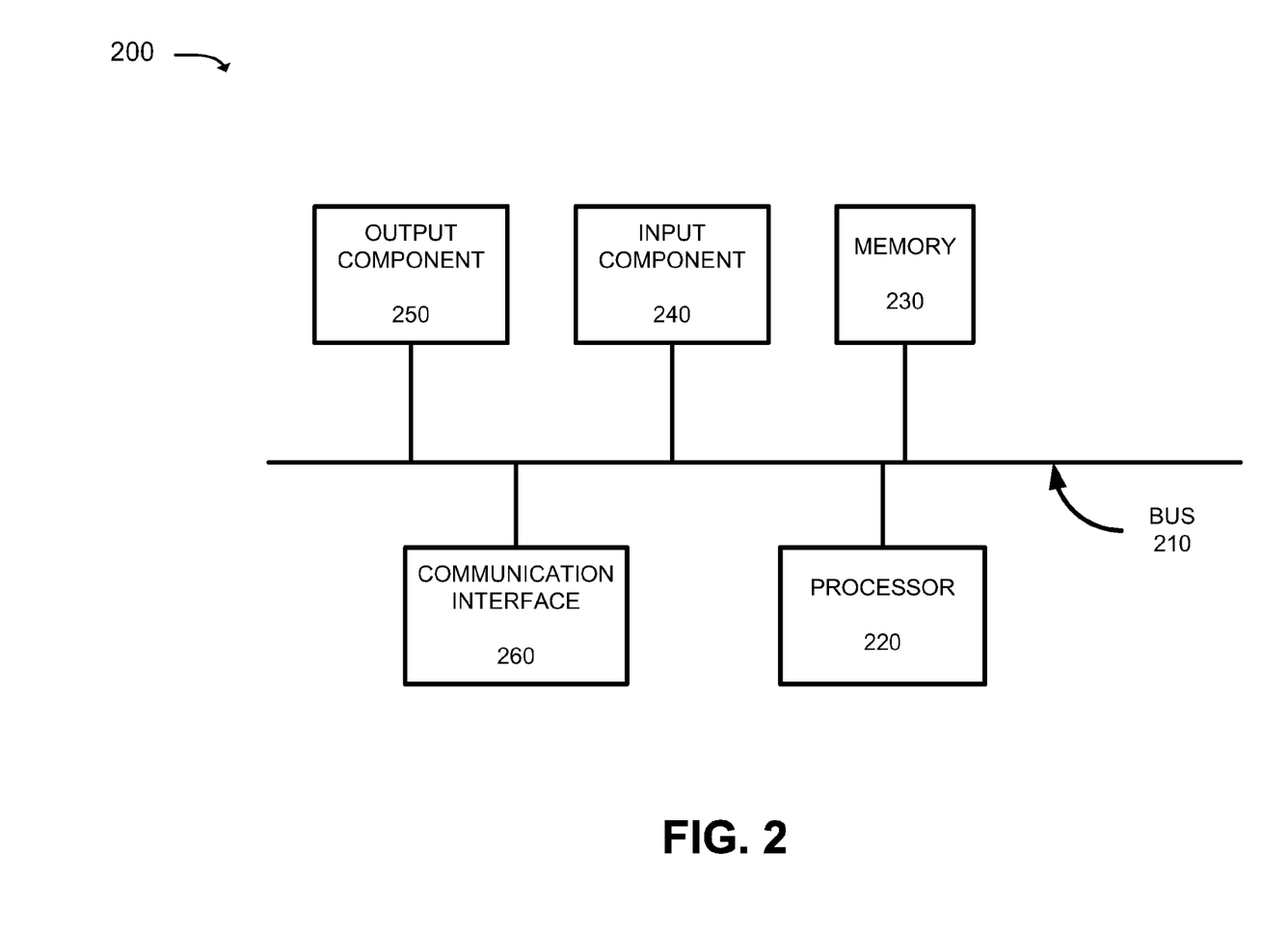
FIG. 2 is a diagram of example components of one or more of the devices of FIG. 1.

FIG. 2 is a diagram of example components of a device 200 that may be associated with user device 110, receiving entity server 120, attributes server 130, and/or verifier server 140. Each one of user device 110, receiving entity server 120, attributes server 130, and/or verifier server 140 may include one or more devices 200 and/or one or more of each one of the components of device 200.

As shown in FIG. 2, device 200 may include a bus 210, a processor 220, a memory 230, an input component 240, an output component 250, and a communication interface 260. In one implementation, device 200 may include additional components, fewer components, different components, and/or differently arranged components than are shown in FIG. 2. Additionally, or alternatively, one or more components of device 200 may perform one or more tasks described as being performed by one or more other components of device 200.

Bus 210 may include a path that permits communication among the components of device 200. Processor 220 may include a processor, a microprocessor, or processing logic that may interpret and execute instructions. Memory 230 may include any type of dynamic storage device that may store information and instructions for execution by processor 220, and/or any type of non-volatile storage device that may store information for use by processor 220.

Input component 240 may include one or more input mechanisms that permit a user to input information to device 200. Output component 250 may include one or more output mechanisms that output information to the user. Examples of input and output mechanisms may include buttons; a touch screen interface to permit data and control commands to be input into device 200; a speaker to receive electrical signals and output audio signals; a microphone to receive audio signals and output electrical signals; a display to output visual information (e.g., web pages, product information, etc.); etc.

Communication interface 260 may include any transceiver-like mechanism that enables device 200 to communicate with other devices and/or systems. For example, communication interface 260 may include an Ethernet interface, an optical interface, a coaxial interface, a wireless interface, or the like.

Device 200 may perform certain operations described herein. Device 200 may perform these operations in response to processor 220 executing software instructions (e.g., computer program(s)) contained in a computer-readable medium, such as memory 230, a secondary storage device (e.g., a hard disk, etc.), or other forms of random access memory (RAM) or read only memory (ROM). A computer-readable medium may be defined as a non-transitory memory device. A memory device may include space within a single physical memory device or spread across multiple physical memory devices. The software instructions may be read into memory 230 from another computer-readable medium or from another device. The software instructions contained in memory 230 may cause processor 220 to perform processes described herein. Alternatively, hardwired circuitry may be used in place of or in combination with software instructions to implement processes described herein. Thus, implementations described herein are not limited to any specific combination of hardware circuitry and software.

Figure 3:
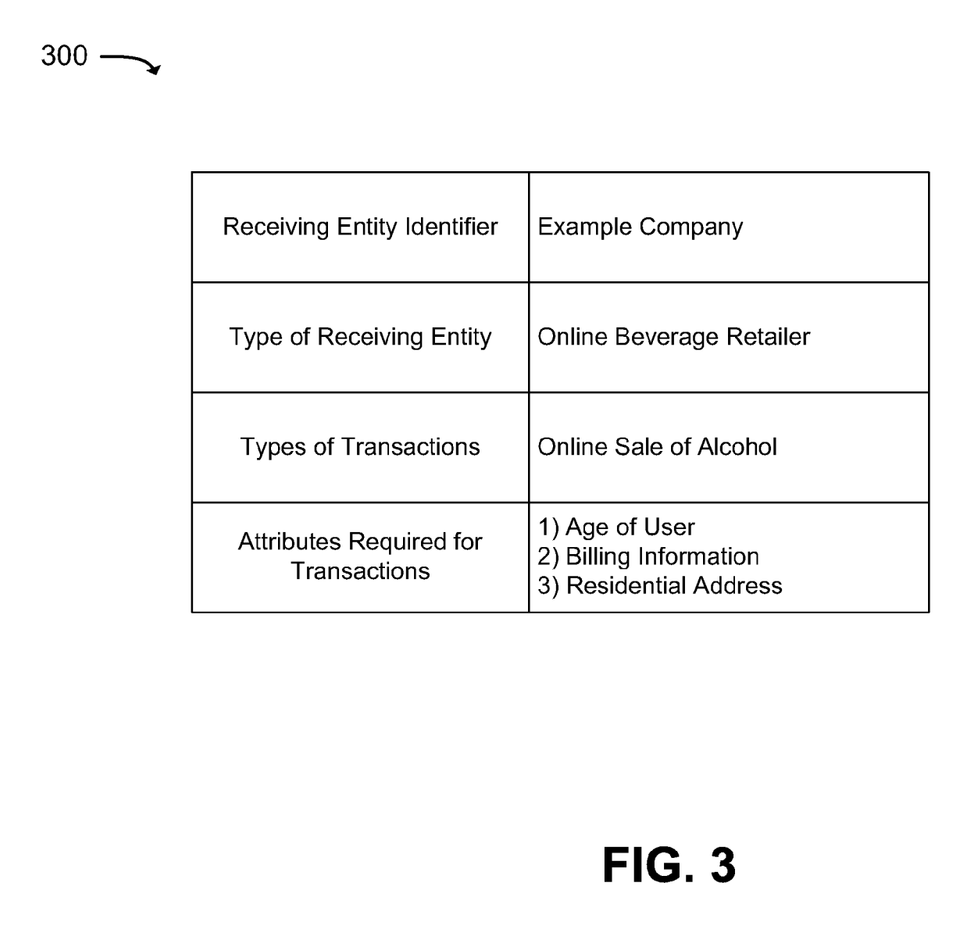
FIG. 3 is a diagram of example information stored for a policy of a receiving entity.

FIG. 3 is a diagram of example information stored for a policy 300 of a receiving entity. As shown in FIG. 3, policy 300 may include a receiving entity identifier field, a type of the receiving entity field, a type of transactions field, and an attributes required for the transactions field. The receiving entity identifier field may include a plurality of characters that uniquely identify the receiving entity associated with policy 300. For example, the receiving entity identifier may include a name of the receiving entity (e.g., Example Company), an address of a website of the receiving entity (e.g., www.example.com), and/or an identifier (e.g., an IP address) associated with receiving entity server 120. A request for attributes, received by attributes server 130 from receiving entity server 120, may include the receiving entity identifier. Attributes server 130 may retrieve policy 300 based on the receiving entity identifier included in the request.

The type of the receiving entity field may include a type (e.g., an online beverage retailer) provided/selected by the receiving entity or by an operator of attributes server 130 when a service relationship is established between the receiving entity and the operator of attributes server 130. In some implementations, the operator of attributes server 130 and/or attributes server 130 may perform due diligence to verify/determine that the receiving entity provides services associated with the type of receiving entity via a website provided by receiving entity server 120 of the receiving entity.

The types of the transactions field may include one or more types of online transactions (e.g., online sale of alcohol) performed by the type of the receiving entity and/or particularly the receiving entity. The receiving entity and/or the operator of attributes server 130 may provide or select the types of the transactions. The operator of attributes server 130 and/or attributes server 130 may perform due diligence to verify/determine that the receiving entity provides the types of the transactions via the website provided by receiving entity server 120.

The attributes required for the transactions field may include one or more attributes of a user (e.g., an age, billing information, and a residential address), of user device 110, that receiving entity server 120 needs to receive in order to complete an online transaction initiated by the user. The receiving entity and/or the operator of attributes server 130 may provide or select the attributes required for the transactions for all the different types of the online transactions, associated with the receiving entity, or for each one of the types of the transactions. The operator of attributes server 130 and/or attributes server 130 may perform due diligence to verify/determine that that receiving entity server 120 requires the attributes, listed as the attributes required for the transactions, to perform online transactions.

In one implementation, after receiving a request for attributes from receiving entity server 120, attributes server 120 may only provide attributes that are included in the attributes required for the transactions field of policy 300. Alternatively, or additionally, attributes server 120 may only provide unnecessary attributes, which are not included in the attributes required for the transactions field of policy 300, after receiving consent from the user to provide the particular unnecessary attributes to the receiving entity and/or to receiving entity server 120.

Figure 4A:
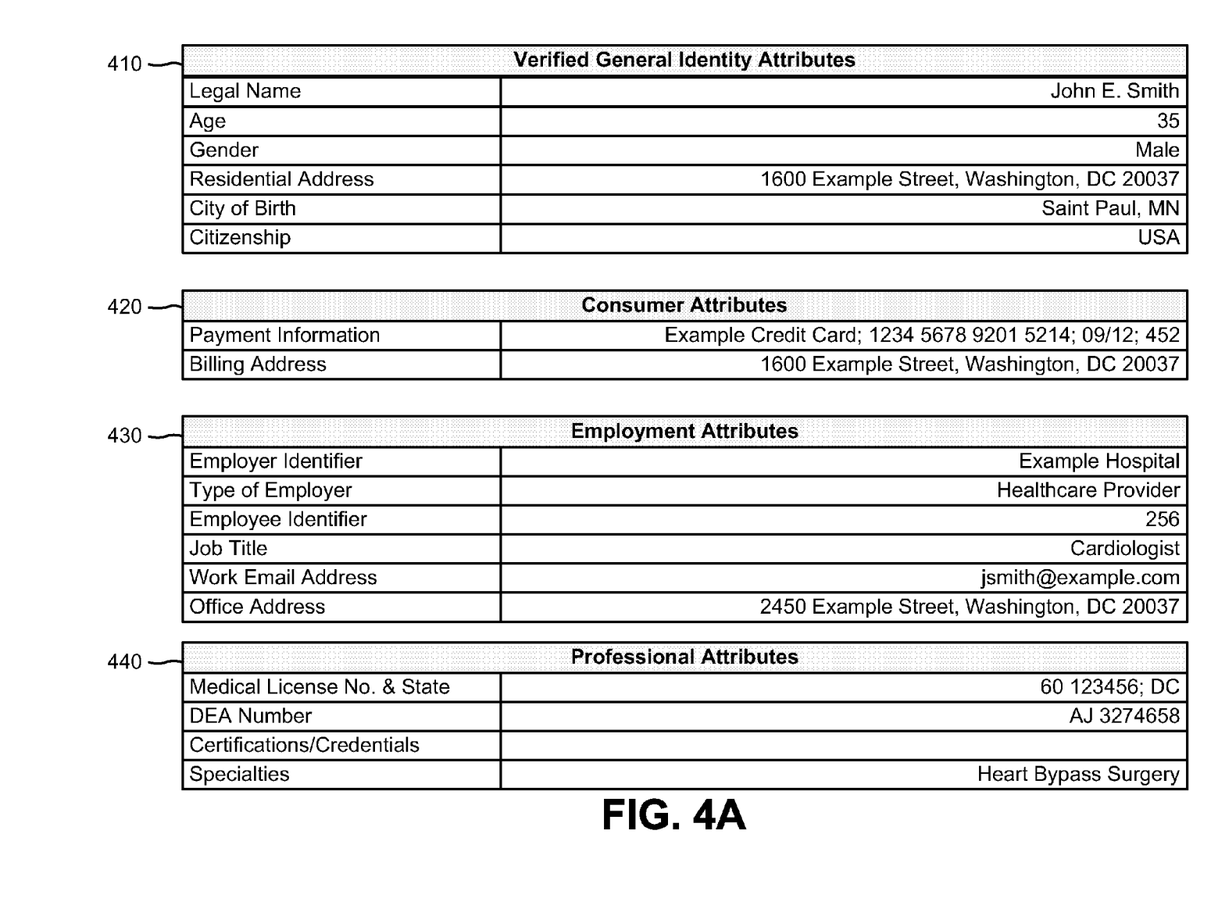
FIGS. 4A and 4B are diagrams of example information stored for attributes of a user.

FIG. 4A is a diagram of example information stored for verified attributes of a user of user device 110. For example, the user may select for attributes server 130 to provide, for the user, different categories of attributes associated with different personas of the user. As shown in FIG. 4A, the different categories of the user may include, for example, verified general identity attributes 410, consumer attributes 420, employment attributes 430, and professional attributes 440. In other implementations, the user may select individual attributes and/or individual attributes for one or more of the categories. Verifier server 140 may provide and/or confirm information used for one or more of verified general identity attributes 410, consumer attributes 420, employment attributes 430, and/or professional attributes 440. Attributes server 130 may not receive information for all attributes selected by the user.

Verified general identity attributes 410 may include attributes that are associated with every person. As shown in FIG. 4A, verified general identity attributes 410 may include, for example, a legal name (e.g., John E. Smith), an age (e.g., 35), a gender (e.g., Male), a residential address (e.g., 1600 Example Street, Washington, D.C. 20037), a city of birth (Saint Paul, Minn.), and citizenship information (e.g., citizen of the USA).

Consumer attributes 420 may include attributes that are associated with an online consumer persona of the user. As shown in FIG. 4A, consumer attributes 420 may include, for example, payment information (e.g., Example Credit Card; 1234 5678 9201 5214; 09/12; 452) and a billing address (e.g., 1600 Example Street, Washington, D.C. 20037).

Employment attributes 430 may include attributes that are associated with an employee persona of the user. Attributes server 130 may determine which attributes are included in employment attributes 430, for the user, based on an employer of the user. As shown in FIG. 4A, employment attributes 430 may include, for example, an employer identifier (e.g., Example Hospital), a type of the employer (e.g., Healthcare Provider), an employee identifier (e.g., 256), a job title (e.g., cardiologist), a work email address (e.g., jsmith@example.com), and an office address (e.g., 2450 Example Street, Washington, D.C. 20037).

Professional attributes 440 may include attributes that are associated with a professional persona of the user. Attributes server 130 may allow the user to select for attributes server 130 to provide professional attributes 440 when attributes server 130 determines that the user is a doctor. As shown in FIG. 4A, professional attributes 440 may include, for example, a medical license number and a state that issued the medical license (e.g., 60 123456; DC), a Drug Enforcement Administration (DEA) number (e.g., AJ 3274658) that is assigned to a health care provider to allow the health care provider to write prescriptions for controlled substances, certifications and/or credentials, and specialties (e.g., Heart Bypass Surgery). In one example, professional attributes 440 may not have information for the certifications and/or credentials attribute because attributes server 130 is unable to receive or verify the information.

Figure 4B:
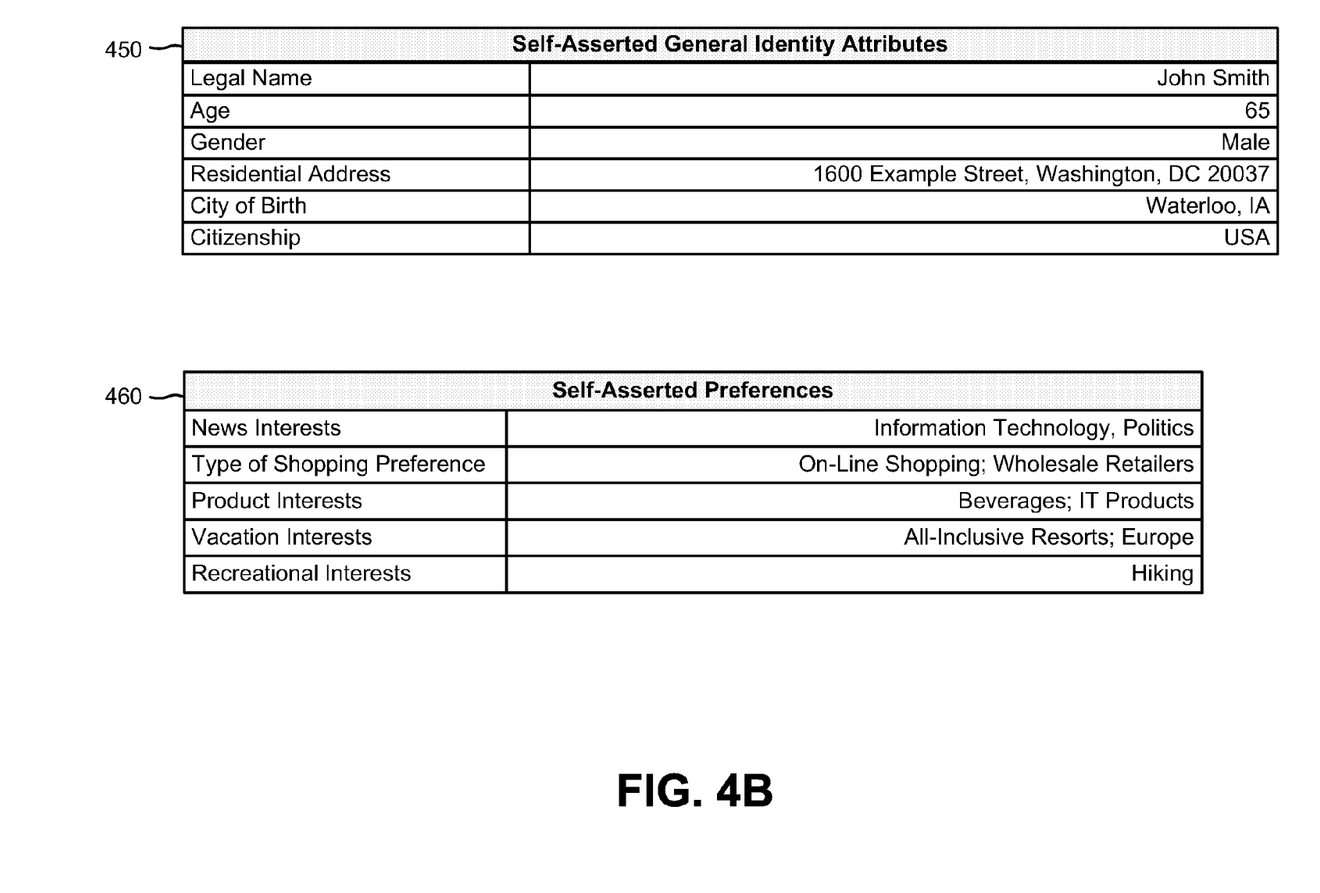

FIG. 4B is a diagram of example information stored for self-asserted attributes of the user of user device 110. The user may select for attributes server 130 to provide, for the user, self-asserted attributes that are different from corresponding verified attributes and/or cannot be verified. As shown in FIG. 4B, the self-asserted attributes that are different from corresponding verified attributes may include, for example, self-asserted general identity attributes 450. Self-asserted general identity attributes 450 may include the same types of attributes as verified general identity attributes 410, including, for example, a legal name, an age, a gender, a residential address, and a citizenship. However, data for the legal name attribute (e.g., John Smith), the age attribute (e.g., 65), and the city of birth attribute (e.g., Waterloo, Iowa), of self-asserted general identity attributes 450, may differ from corresponding verified attributes of verified general identity attributes 410.

As shown in FIG. 4B, self-asserted attributes that cannot be verified may include, for example, self-asserted preferences 460. Attributes server 130 may not store verified attributes that correspond to self-asserted preferences 460. Self-asserted preferences 460 may include, for example, news interests (e.g., Information Technology (IT); Politics), type of shopping preference (e.g., on-line shopping; wholesale retailers), product interests (e.g., beverages; IT products), vacation interests (e.g., all-inclusive resorts; Europe), and recreational interests (e.g., hiking).

Figure 5:
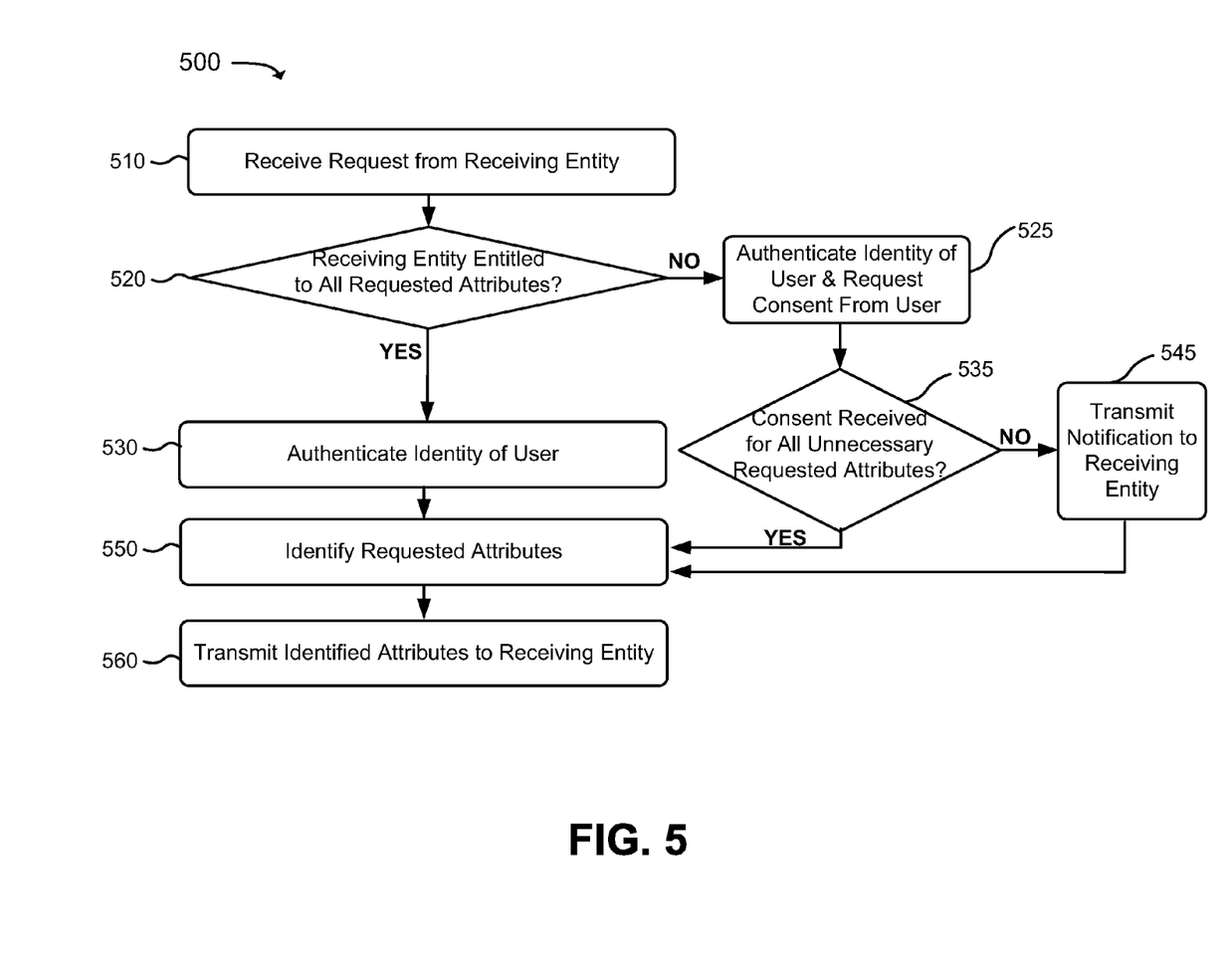
FIG. 5 is a flow chart of an example process for providing attributes of a user.

FIG. 5 is a flow chart of an example process 500 for providing attributes of a user. In one implementation, attributes server 130 may perform process 500. Alternatively, or additionally, a device or collection of devices separate from, or in combination with, attributes server 130 may perform some or all of process 500. A portion of process 500 is described below with reference to FIGS. 6A and 6B.

As shown in FIG. 5, process 500 may include receiving a request from a receiving entity (block 510). For example, a user may access a website of a receiving entity (e.g., an online alcohol beverage retailer) via a browser of user device 110. The user may use user device 110 to initiate an online transaction (e.g., purchase an alcoholic product by selecting the alcoholic product and pressing a "Buy" button) via the website. In response, user device 110 may transmit an online transaction request 610 (FIGS. 6A and 6B) to receiving entity server 120 that provides the website. Receiving entity server 120 may determine, for example, that the receiving entity needs to verify an age of the user and receive payment information and a shipping address in order to process/complete the online transaction. Receiving entity server 120 may further determine, for example, that the receiving entity needs a self-asserted age attribute of the user in order to select targeted advertisements for the user.

Figure 6A:
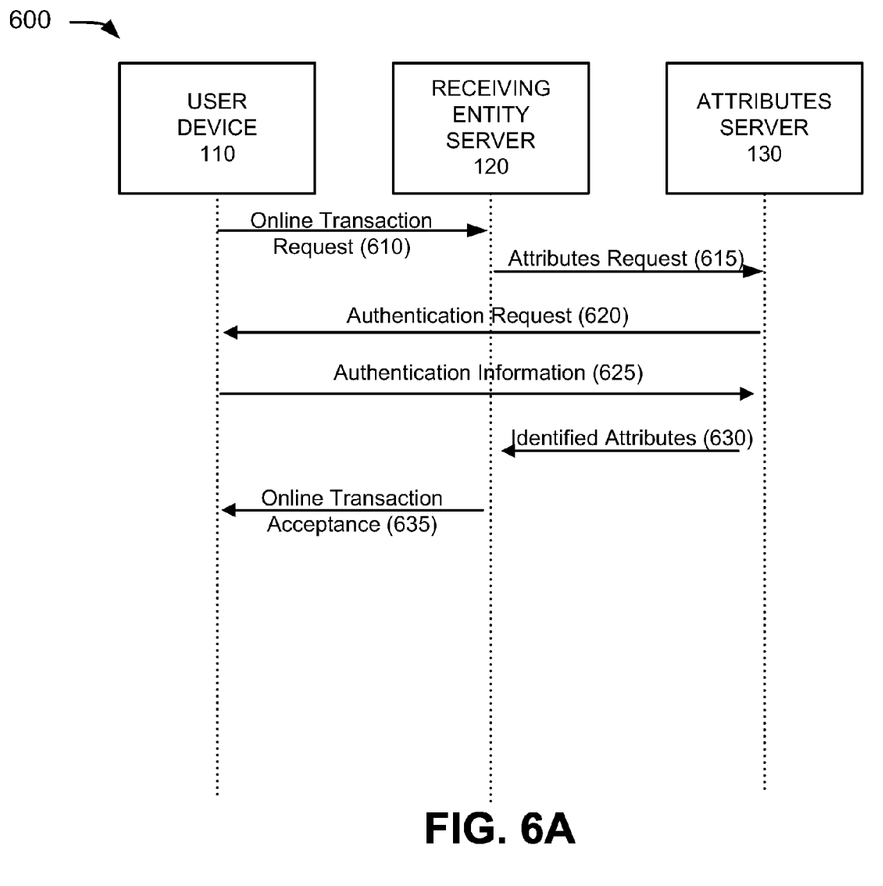
FIGS. 6A and 6B are flow diagrams of examples of providing attributes of the user.
Figure 6B:
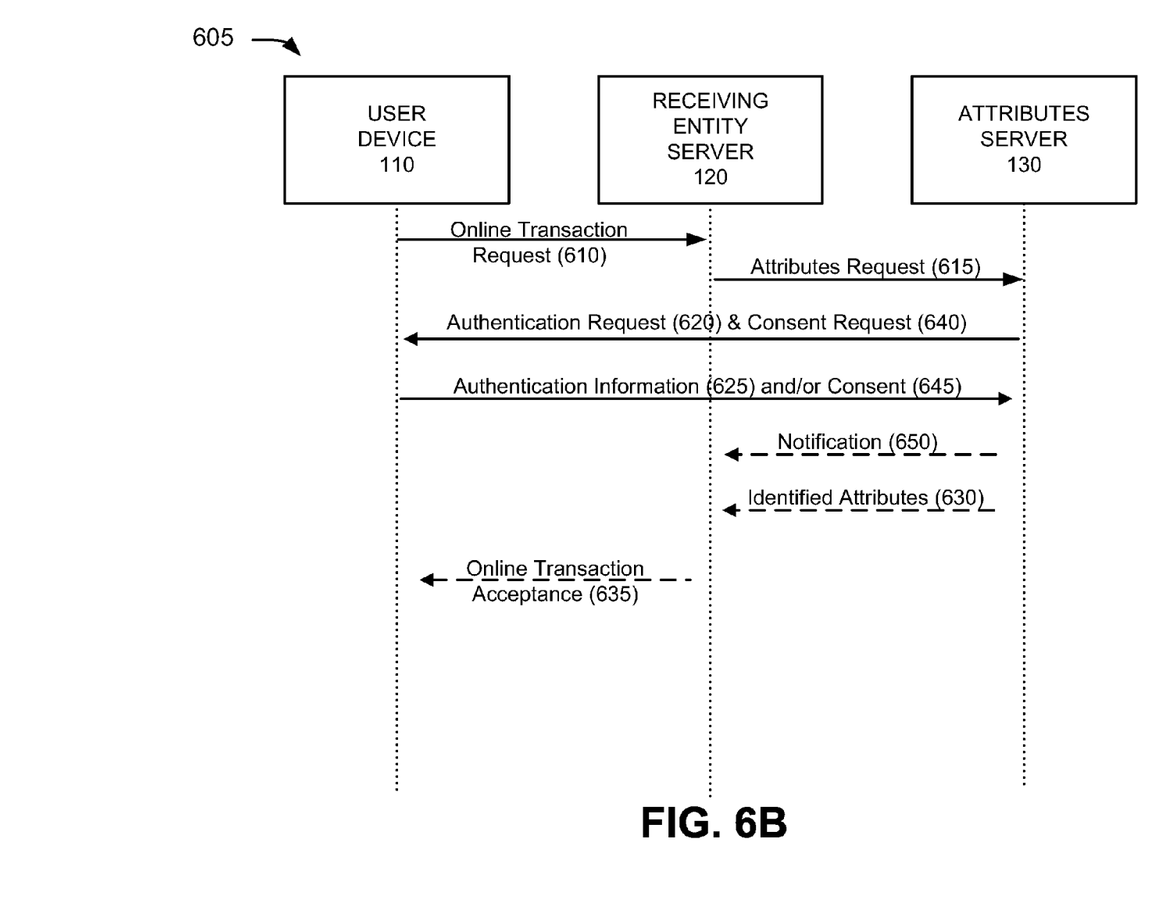

Receiving entity server 120 may generate an attributes request 615 (FIGS. 6A and 6B). Attributes request 615 may include an identifier associated with the receiving entity and/or receiving entity server 120; an IP address of the browser; and a request for a verified age attribute, a verified payment information attribute, a verified residential address attribute, and a self-asserted age attribute of the user. Receiving entity server 120 may transmit attributes request 615 to attributes server 130. Attributes server 130 may receive attributes request 615 from receiving entity server 120.

Process 500 may further include determining whether the receiving entity is entitled to all requested attributes (block 520). For example, attributes server 130 may retrieve a policy of the receiving entity based on the identifier included in attributes request 615. Attributes server 130 may determine that the receiving entity is entitled to attributes requested in attributes request 615 when the policy specifies that the receiving entity is entitled to those requested attributes. Further to the example above, assume that the policy indicates that the receiving entity (e.g., receiving entity server 120) is entitled to receive, for example, an age attribute, a payment information attribute, and a residential address for a customer. Accordingly, attributes server 130 may determine that receiving entity server 120 is entitled to receive the verified age attribute, the verified payment information attribute, and the verified residential address attribute of the user. Attributes server 130 may further determine that receiving entity server 120 is not entitled to receive the self-asserted age attribute because the self-asserted age attribute is not necessary for the receiving entity to complete the online transaction.

If attributes server 130 determines that the receiving entity is entitled to all the requested attributes (block 520—YES), process 500 may include authenticating an identity of a user (block 530). For example, after determining that the receiving entity is entitled to all the requested attributes, requested in attributes request 615, attributes server 130 may determine whether an identity of the user is already authenticated based on the IP address included in attributes request 615. If the identity of the user is not already authenticated, attributes server 130 may transmit an authentication request 620 (FIG. 6A) to the browser of user device 110 based on the IP address. Authentication request 620 may include a dialog box for receiving authentication information 625 (FIG. 6A) from the user. The user may use user device 110 to enter authentication information 625 via the dialog box. Authentication information 625 may include, for example, a username and/or a password of the user. Attributes server 130 may receive authentication information 625 from user device 110. Attributes server 130 may authenticate the identity of the user based on authentication information 625.

If attributes server 130 determines that the receiving entity is not entitled to all the requested attributes (block 520—NO), process 500 may include authenticating an identity of a user and requesting consent from the user (block 525) and determining whether the consent is received for all unnecessary requested attributes (block 535). For example, after determining that the receiving entity is not entitled to all the requested attributes, requested in attributes request 615, attributes server 130 may generate a consent request 640 (FIG. 6B) to request consent to provide, to the receiving entity, one or more unnecessary requested attributes, of the user, that are not necessary for receiving entity server 120 to complete the online transaction. Attributes server 130 may transmit authentication request 620 and consent request 640 (FIG. 6B) to user device 110 based on the IP address included in attributes request 615. Consent request 640 may include a dialog box that allows the user to consent to provide, to the receiving entity, one or more of the unnecessary requested attributes, of the user, that are not necessary for receiving entity server 120 to complete the online transaction. After entering authentication information 625, the user may use user device 110 to enter a consent 645 (FIG. 6B) to provide one or more of the unnecessary requested attributes to receiving entity server 120. User device 110 may transmit authentication information 625 and consent 645 when the user enters consent 645. Attributes server 130 may receive authentication information 625 and/or consent 645 from user device 110. Attributes server 130 may determine whether consent 645 is received for all unnecessary requested attributes.

If consent is not received for all the unnecessary requested attributes (block 535—NO), process 500 may include transmitting a notification to the receiving entity (block 545). For example, attributes server 130 may determine that consent 645 is not received for all the unnecessary requested attributes when the user enters consent 645 for less than all the unnecessary requested attributes. Thereafter, attributes server 130 may transmit a notification 650 (FIG. 6B) to receiving entity server 120. Notification 650 may indicate for which unnecessary requested attributes the user of user device 110 did not enter consent. Further to the example above, assume that the user does not enter consent to provide the self-asserted age attribute to receiving entity server 120. Consent 645 may indicate that the user did not enter consent for the self-asserted age attribute (i.e., did not enter consent for any unnecessary requested attribute). Attributes server 130 may transmit notification 650, which indicates that the user did not enter consent for the self-asserted age attribute, to receiving entity server 120.

After authenticating an identity of the user (block 530), if the consent is received (block 535—YES), or after transmitting the notification to the receiving entity (block 545), process 500 may include identifying the requested attributes (block 550). For example, authenticating the identity of the user may include associating attributes stored for the user with the IP address included in attributes request 615 based on the authenticated identity. Attributes server 130 may identify one or more of the requested attributes, identified attributes 630 (FIGS. 6A and 6B), from attributes associated with the user. When attributes server 130 determines that the receiving entity is entitled to all the requested or attributes or when attributes server 130 determines that consent 645 is received for all the unnecessary requested attributes, identified attributes 630 may include all the requested attributes. When consent is not received for all the unnecessary requested attributes, identified attributes 630 may include only the requested attributes that are necessary or for which consent 645 is provided.

Further to the example above, identified attributes 630 may include only the verified age attribute, the verified payment information attribute, and the verified residential address attribute in identified attributes 630. Identified attributes 630 may not identify and include, in identified attributes 630, the self-asserted age attribute because the self-asserted age attribute is an unnecessary requested attribute and because the user did not enter consent 645 for the self-asserted age attribute.

As further shown in FIG. 5, process 500 may include transmitting identified attributes to the receiving entity (block 560). For example, attributes server 130 may transmit identified attributes 630 to receiving entity server 120. Receiving entity server 120 may process online transaction request 610 and/or complete the online transaction based on identified attributes 630. Further to the example above, receiving entity server 120 may determine that the user is above a particular age (e.g., 21) based on the verified age attribute, charge the user for the alcoholic product based on the verified payment information, and plan to ship the alcoholic product to the verified residential address.

In one implementation, attributes server 130 may transmit identified attributes 630 and notification 650 at the same time. In other implementations, online transaction request 610 may include attributes provided by the user (e.g., including an age, payment information, and/or an address). Attributes request 615 may include a request to confirm the provided attributes based on corresponding verified attributes instead of a request to receive the verified attributes (e.g., the verified age attribute, the verified payment information attribute, the residential address attribute). Attributes server 130 may transmit a confirmation that specifies which ones of the provided attributes are accurate (e.g., match corresponding verified attributes) instead of, or in addition to, transmitting identified attributes 630. Receiving entity server 120 may process online transaction request 610 after determining that the confirmation indicates that the provided attributes are accurate.

Alternatively, or additionally, authenticating the identity of the user (block 530 or block 525) may further include determining a geographic location of user device 110 and a geographic location of a mobile device (not shown in FIG. 1) of the user. The mobile device may be different from user device 110. In one example, attributes server 130 may only authenticate the identity of the user when the geographic location of user device 110 is within a particular distance of the geographic location of the mobile device. This may allow attributes server 130 to verify that the user is the one who is actually using user device 110 to initiate the online transaction.

Alternatively, or additionally, attributes server 130 may require the user to provide additional authentication information (e.g., a personal identification number (PIN)), before the identity of the user is authenticated, when the geographic location of user device 110 is not within the particular distance of the geographic location of the mobile device. In yet another example, attributes server 130 may only provide particular types of attributes (e.g., a gender) and/or not provide other types of attributes (e.g., a social security number (SSN)) when the geographic location of user device 110 is not within the particular distance of the geographic location of the mobile device.

As further shown in FIGS. 6A and 6B, after process 500, receiving entity server 120 may transmit an online transaction acceptance 635 that indicates that the online transaction has successfully been completed. Further to the example above, transaction acceptance 635 may indicate that the alcoholic product is purchased and will be shipped to the verified residential address of the user.

Although implementations are described above with reference to online transactions, similar approaches and/or techniques may be used for offline transactions (e.g., transactions that are not initiated online). For example, assume that a user decides to purchase alcohol at a physical store location. The user may proceed to the store and select the alcohol for purchase. An employee of the store may request for the user to provide a verified age attribute of the user. To do so, the user may place user device 110 (e.g., a mobile phone device) next to a point of sale (POS) device of the store.

In one implementation, the POS device may transmit a request for the age attribute of the user to user device 110. User device 110 may determine whether the POS device is entitled to receive the age attribute. If user device 110 determines that the POS device is entitled to receive the requested age attribute, user device 110 may provide the age of the user and/or confirm that the user is over a particular age (e.g., 21 years old). In another implementation, after receiving the request for the age attribute of the user, user device 110 may transmit instructions to attributes server 130 for attributes server 130 to provide the age attribute of the user to the POS device.

In yet another implementation, the POS device may receive an identifier associated with the user from user device 110. The POS device may generate the request for the age attribute based on the identifier, and may transmit the request for the age attribute, of the user associated with the identifier, to attributes server 130. Attributes server 130 may determine whether the POS device of the store is entitled to receive the age attribute. If attributes server 130 determines that the POS device is entitled to receive the requested age attribute, attributes server 130 may provide the age of the user and/or confirm that the user is over a particular age (e.g., 21 years old).

The POS device may receive the verified age attribute for the user, and may communicate (e.g., display) information (e.g., the age) to the employee that indicates whether the user is allowed to purchase the alcohol. The employee of the store may decide to complete the offline transaction (i.e., sell the alcohol) based on the information. For example, the employee may sell the alcohol to the user when the information indicates that the user is over the particular age.

The foregoing description provides illustration and description, but is not intended to be exhaustive or to limit the embodiments to the precise form disclosed. Modifications and variations are possible in light of the above teachings or may be acquired from practice of the embodiments.

While a series of blocks has been described with regard to FIG. 5, the order of the blocks may be modified in other implementations. Further, non-dependent blocks may be performed in parallel.

It will be apparent that systems and methods, as described above, may be implemented in many different forms of software, firmware, and hardware in the implementations illustrated in the figures. The actual software code or specialized control hardware used to implement these systems and methods is not limiting of the implementations. Thus, the operation and behavior of the systems and methods were described without reference to the specific software code—it being understood that software and control hardware can be designed to implement the systems and methods based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the implementations includes each dependent claim in combination with every other claim in the claim set.

No element, act, or instruction used in the present application should be construed as critical or essential to the implementations unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
   receiving, by a first server device, a request for information from a second server device of a receiving entity,
      wherein the request for information corresponds to a plurality of attributes and are independently-verified attribute data and attribute data self-asserted by a user, corresponding to a same one of the attributes, differ, and
      wherein the request for information is related to a transaction between the user and the receiving entity;
   receiving, by the first server device, policy information associated with the receiving entity,
      wherein the policy information is based upon the type of the receiving entity and the type of transaction;
   determining, by the first server device, that the receiving entity is entitled to receive the information corresponding to at least one of the requested attributes that is required to process the transaction;
   determining, by the first server device, that the receiving entity is not entitled to receive the information corresponding to one or more of the requested attributes that are not necessary to process the transaction;
   based on a determination that the receiving entity is entitled to receive the information corresponding to at least one of the requested attributes that is required to process the transaction, authenticating, an identify of the user;
   based on a determination that the receiving entity is not entitled to receive the information corresponding to at least one of the requested attributes that is required to process the transaction, generating a request for the user's consent to provide the information corresponding to the one or more of the requested attributes to the receiving entity;
   receiving, by the first server device, user's consent to provide the information corresponding to the one or more of the requested attributes to the receiving entity;
   determining, by the first server device, that the user's consent to provide the information corresponding to the one or more of the requested attributes to the receiving entity, was not received;

based on a determination that the user's consent to provide the information corresponding to the one or more of the requested attributes to the receiving entity, was not received, transmitting notification to the second server device;

identifying, by the first server device, the information corresponding to the at least one necessary attribute, based on the authenticated identity, that the receiving entity is entitled to receive;

identifying, by the first server device, the information corresponding to the one or more of the unnecessary attributes for which consent is received from the user; and transmitting, by the first server device, the identified information to the second server device.

2. The method of claim 1, receiving the request for the information corresponding to the plurality of attributes, comprising one or more of:

receiving a request for an age of the user, receiving a request for a gender of the user, receiving a request for an address of the user, or receiving a request for one or more professional attributes associated with a profession identified with the user.

3. The method of claim 1, receiving the request from the second server device of the receiving entity, comprising one of:

receiving the request from the second server device of an online merchant, receiving the request from the second server device of a service provider, or receiving the request from the second server device of a government agency.

4. The method of claim 1, further comprising:

associating the request for the information corresponding to the plurality of attributes with an online transaction between the receiving entity and the user, in which:

the online transaction is one of an online purchase or a request for information.

5. The method of claim 1, further comprising:

receiving permission to provide the information corresponding to a particular type of attribute to the receiving entity;

requesting the information corresponding to a verified attribute of the particular type of attribute from a third server device; and receiving, before receiving the request for the information corresponding to the plurality of attributes, the information corresponding to the verified attribute from the third server device, where the verified attribute is one of the identified attributes.

6. The method of claim 1, further comprising:

determining a type of the receiving entity;

determining types of attributes that are required, for the second server device to process online transactions, based on the type of the receiving entity; and creating a policy for the receiving entity based on the types of attributes that are required.

7. The method of claim 6, determining that the receiving entity is entitled to receive the information corresponding to the at least one attribute, comprising:

determining that the receiving entity is entitled to receive the information corresponding to the attributes that are of the types of attributes specified in the policy.

8. The method of claim 1, further comprising:

determining whether consent is received from the user in response to the request for the user's consent; and not identifying the information corresponding to a first attribute of the one or more of the unnecessary attributes for which consent is not received to provide the information corresponding to the first attribute of the one or more unnecessary attributes to the receiving entity.

9. The method of claim 8, further comprising:

transmitting a notification to the second server device that the consent is not received for the information corresponding to the first attribute of the one or more unnecessary attributes.

* * * * *